United States Patent [19]
Williams et al.

[11] Patent Number: 5,988,444
[45] Date of Patent: *Nov. 23, 1999

[54] DENTAL PRODUCT

[75] Inventors: David Robert Williams, Monroe; Stephen Roy Barrow, Trumbull; Jesus Antonio Urbaez, Waterbury; Christine Watson Ryles, Milford, all of Conn.

[73] Assignee: Chesebrough-Pond's USA Co., Greenwich, Conn.

[*] Notice: This patent is subject to a terminal disclaimer.

[21] Appl. No.: 09/227,752

[22] Filed: Jan. 8, 1999

Related U.S. Application Data

[62] Division of application No. 08/912,252, Aug. 15, 1997
[60] Provisional application No. 60/032,033, Nov. 26, 1996.

[51] Int. Cl.⁶ .................................................. B67D 5/52
[52] U.S. Cl. ...................................... 222/137; 222/145.3
[58] Field of Search ................................. 222/137, 145.3

[56] References Cited

U.S. PATENT DOCUMENTS

| | | |
|---|---|---|
| 4,528,180 | 7/1985 | Schaeffer . |
| 4,627,977 | 12/1986 | Gaffar et al. . |
| 4,687,663 | 8/1987 | Schaeffer . |
| 4,849,213 | 7/1989 | Schaeffer . |
| 5,020,694 | 6/1991 | Pettengill . |
| 5,038,963 | 8/1991 | Pettengill et al. . |
| 5,335,827 | 8/1994 | Gentile . |

*Primary Examiner*—Gregory L. Huson
*Attorney, Agent, or Firm*—Milton L. Honig

[57] ABSTRACT

A dental product is provided packaged in a telescopically arranged multi-cavity dispensing container having at least two cylinders in an upper body thereof. Peroxide and baking soda are placed as active ingredients in separate respective semi-solid streams, each stream being in separate ones of the cylinders. Uniform dispensing of each stream to deliver relatively equivalent ribbon length of each stream by incorporating a synthetic linear anionic polycarboxylate to adjust viscosity. Preferred polycarboxylates are homopolymers of acrylic, methacrylic and maleic acids, most especially a copolymer of vinyl methyl ether and maleic acid or anhydride.

7 Claims, 1 Drawing Sheet

U.S. Patent  Nov. 23, 1999  5,988,444
FIG.
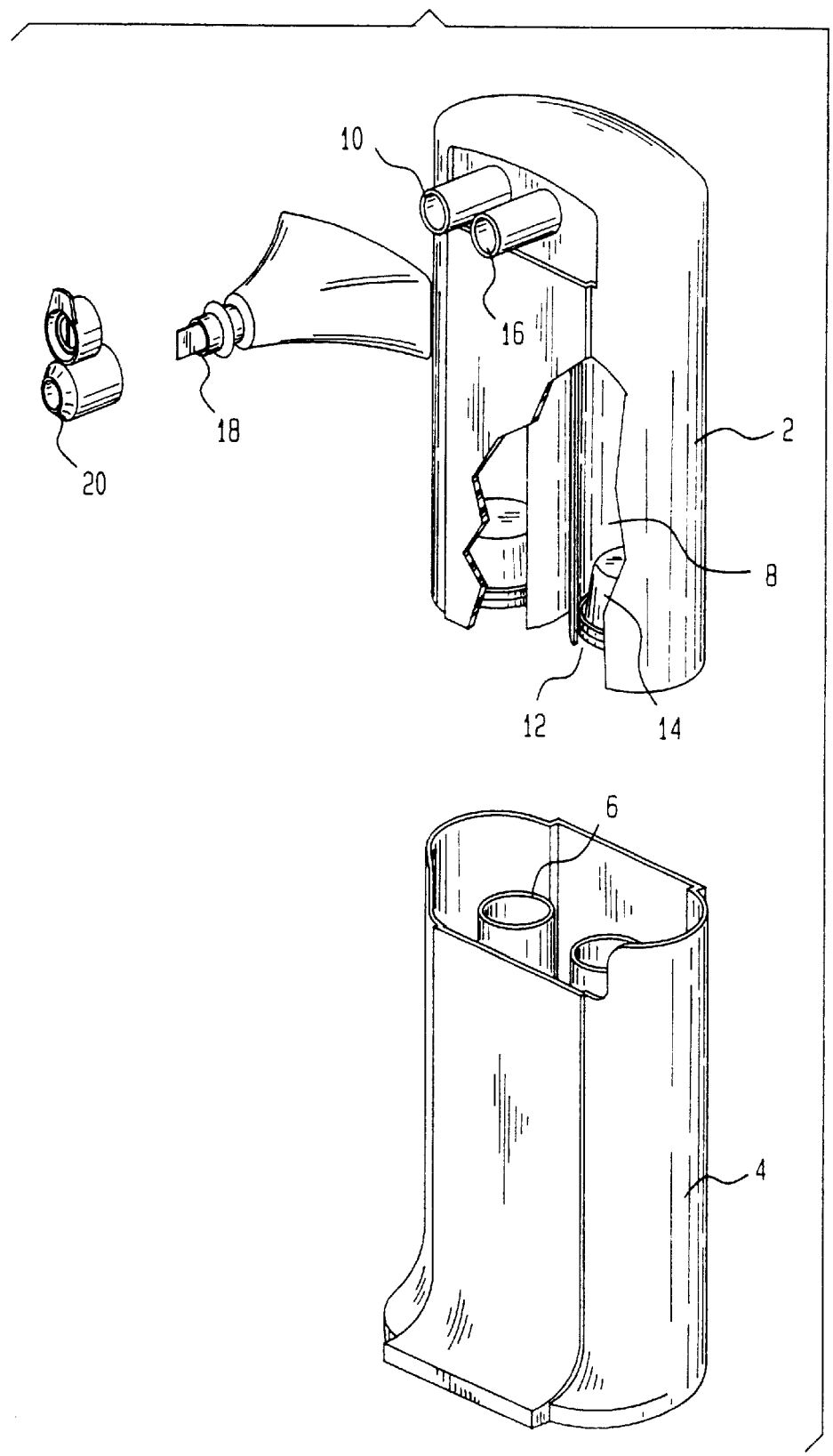

DENTAL PRODUCT

This is a divisional of Provisional Appln. No. 60/032,033 filed Nov. 26, 1996 completed as Ser. No. 08/912,252 filed Aug. 15, 1997.

BACKGROUND OF THE INVENTION

1. Field of the Invention

The invention relates to a dental product, more particularly a telescopically arranged multi-cavity dispensing container two of which cavities are filled with semi-solid dentifrice compositions respectively containing peroxide and baking soda as active ingredients.

2. The Related Art

Oral compositions with peroxide and baking soda (i.e. sodium bicarbonate) have become commercially quite popular. The combination of actives has been reported to promote healthy gums. When in contact, peroxide and baking soda are reactive towards one another. Therefore these ingredients must be maintained separately until time of use. Dispensing packages have been developed which physically isolate peroxide and baking soda by separating them into different compartments. This approach has been described in a series of patents to Schaeffer including U.S. Pat. No. 4,849,213, U.S. Pat. No. 4,528,180 and U.S. Pat. No. 4,687,663.

Dosing of flavor, fluoride and other actives has always been a challenge from multi-compartment dispensers that simultaneously extrude more than one stream of toothpaste. Unequal dispensing may adversely effect taste, aesthetics and oral hygiene. The most successful package for controlled delivery has been a telescopically arranged multi-cavity dispensing pump, especially as described in U.S. Pat. No. 5,020,694 and U.S. Pat. No. 5,038,963 and U.S. Pat. No. 5,335,827 (relating to a refill cartridge), all of which are herein incorporated by reference. Commercially the pump is embodied in Mentadent Peroxide and Baking Soda toothpaste.

Consumers have noted that even with telescoping pumps it is often difficult to extrude equal lengths of respective peroxide and baking soda dentifrice ribbons.

Accordingly, it is an object of the present invention to provide a peroxide and baking soda dental product based on a telescopically arranged multi-cavity dispensing container wherein essentially identical toothpaste ribbons from each of the cavities can be dispensed.

Another object of the present invention is to provide a peroxide and baking soda dental product packaged in a telescopically arranged multi-cavity dispensing container wherein viscosity of each cavity stream can be better controlled thereby allowing more accurate dosing.

These and other objects of the present invention will become more readily apparent from consideration of the following summary and detailed discussion.

SUMMARY OF THE INVENTION

A dental product is provided including:
(i) a dispensing container with an upper and a lower body which are telescopically engageable one with another, the upper body including at least two hollow and separate cylinders, the cylinders having a first generally closed end and a second end telescopically and slidingly accommodating at least two parallel pistons which conform to ride sealingly along the interior walls of the cylinders so as to force any flowable materials to flow toward the first end of the cylinder upon relative compression of the cylinders and pistons, the cylinders having outlet channels;
(ii) an outlet mechanism in fluid communication with the outlet channels, the outlet mechanism including adjacent outlet openings unconnected to each other and having means for causing the flowable materials to flow toward each other at the outlet openings to form a single, banded, unmixed stream;
(iii) a first semi-solid flowable material containing a peroxide and a second semi-solid flowable material containing a bicarbonate salt, each of the first and second semi-solid materials being stored in separate ones of the at least two hollow parallel cylinders, at least one of the semi-solid materials containing from 0.05 to 20% of a synthetic anionic linear polymeric polycarboxylate.

BRIEF DESCRIPTION OF THE DRAWING

The above features, advantages and objects of the present invention will more fully be appreciated through the following detailed discussion, reference being made to the drawing consisting of a single FIGURE which is an expanded view of a telescopically arranged multi-cavity dispensing pump.

DETAILED DISCUSSION

Now it has been found that in the context of telescopically arranged multi-cavity dispensing pumps, control of the flowable toothpaste contents can be obtained through use of synthetic anionic linear polymeric polycarboxylates in the formulation. Polycarboxylates allow for close matching of flow properties between a peroxide and a baking soda active containing stream. Flavors, fluoride and actives formulated in either or both of the flowable streams, can therefore be dosage regulated with high accuracy. Both streams can be extruded with much better control.

The dispensing container of the present invention as shown in the FIGURE includes an upper body 2 and a lower 4, the former telescopically engaging within the latter. Within the lower body 4 are a pair of parallel piston rods 6 rigidly standing, and preferably unitarily molded with the lower body. These rods may be hollow or solid. While the depicted configuration is round, the rods may be rectangular or of any other polygonal shape.

Upper body 2 includes a pair of separate parallel cylinders 8 each having a first generally closed end 10 and a second end 12 telescopically and slidingly accommodating piston heads 14. These heads conform to ride sealingly along interior walls of the cylinders so as to force flowable materials to flow towards the first end of the cylinder. The cylinder walls may be formed as part of the upper body or may be formed as refill cartridges separate and removable from the upper body. Activation of flow is accomplished by hand pressure downward on the top of the upper body which pressure forces the upper body to telescopically descend within the lower body. Movement of the bodies causes pistons 6 against each of the respective piston heads 14 to move upward along respective cylinders 8. Flowable material in each of the cylinders is then forced through a pair of outlet channels 16. Flowable toothpaste exits the outlet channels passing in unmixed streams through an outlet nozzle having a septum 18 maintaining respective toothpastes in unmixed relationship to outlet openings 20.

First and second semi-solid extrudable streams of dentifrice will be stored in each of the respective cylinders 8. The first of the streams will include a peroxide component such as an alkali metal perborate, percarbonate, urea peroxide, persilicate, perphosphate, calcium peroxide or hydrogen peroxide. Most suitable for this invention is hydrogen peroxide. Amounts of the peroxide may range from 0.01 to 15%, preferably from 0.5 to 3% by weight of the first material.

The peroxide containing composition may either be a paste or gel, preferably the latter. When a gel, water will be present in amounts ranging from 20 to 70%, preferably from 30 to 55%, optimally between 30 to 40% by weight of the first material.

For anti-caries protection, a source of fluoride ion will normally be present in one or both of the flowable materials of the total oral composition. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3% by weight, preferably 0.2 to 0.6% by weight of the total oral composition.

Essential for the present invention are synthetic anionic linear polymeric polycarboxylates. The synthetic anionic linear polymeric polycarboxylates operative herein are well known, being employed in the form of their partially or preferably fully neutralized water soluble alkali metal (e.g. potassium or sodium) or ammonium salts. Preferred are 1:4 to 4:1 copolymers of maleic anhydride or acid with another polymerizable ethylenically unsaturated monomer, especially methyl vinyl ether (methoxyethylene) having a molecular weight (M.W.) of about 10,000 to about 1,000,000. These copolymers are commercially available as Gantrez AN 139 (M.W. 500,000), A.N. 119 (M.W. 250,000) and preferably S-97 (M.W. 70,000), from ISP Corporation. The terms "synthetic" and "linear" are intended to exclude known thickening or gelling agents comprising carboxymethylcellulose and other derivatives of cellulose and natural gums, as well as the Carbopols which are cross-linked.

Other operative polymeric polycarboxylates include those disclosed in U.S. Pat. No. 3,956,180 herein incorporated by reference, such as the 1:1 copolymers of maleic anhydride with ethyl acrylate, hydroxyethyl methacrylate, N-vinyl-2-pyrrolidone, or ethylene, the latter being commercially available as Monsanto EMA No. 1103 (M.W. 10,000) and EMA No. 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. Nos. 4,138,477 and 4,183,914, herein incorporated by reference, which include copolymers of maleic anhydride with styrene, isobutylene or ethyl vinyl ether, polyacrylic, polyitaconic and polymaleic acids, and sulfoacrylic oligomers of M.W. it as low as 1,000, available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorosorbic, cinnamic, beta-styrilactylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anydrides. Other different olefinic monomers copolymerizable with such carboxylic monomers include vinylacetate, vinyl chloride, dimethyl maleate and the like. Copolymers should contain sufficient carboxylic salt groups for water-solubility.

The synthetic anionic linear polymeric polycarboxylate component is mainly a hydrocarbon with optional halogen and O-containing substituents and linkages a as present in ester, ether and OH groups, and is generally employed in the instant compositions in approximate weight amounts of 0.05 to 20%, preferably 0.05 to 5%, more preferably 0.1 to 2%.

Viscosity as measured on a Brookfield RVT, E Bar 2.5 RPM, for each of the 1i semi-solid material streams may range from 20,000 to 1,500,000 centipoise, preferably from 50,000 to 800,000 centipoise at 25° C.

A variety of other ingredients normally present in dentifrices can be selected for the semi-solid streams of peroxide and bicarbonate of the present invention. When the semi-solid is a gel, it is usual to employ a thickening agent with the water that is a cross-linked acrylic polymer. Alternatively and most preferably gels can be structured with a polyoxyethylene-polyoxypropylene copolymer. Commercially, the copolymers are available from the BASF Corporation under the trademark Pluronic F88, F99, F108 and F127. Most preferred is Pluronic F127 (more commonly described by its CTFA name, Poloxamer 407) which has a molecular weight ranging from 10,000 to 15,000, and containing 70% of the hydrophilic polyoxyethylene moiety. Amounts of the copolymer can range anywhere from 18–25% by weight, preferably between 19 and 24%. Poloxamers are particularly suitable for this invention because of their wide pH tolerance, high compatibility with hydrogen peroxide and unique gel properties.

Advantageously, glycerol should also be present in the gel component in an amount from 15 to 60%, preferably in an amount greater than 30% but less than 50%, optimally between 35 to 45% by weight of the gel component.

A low pH, preferably a pH no higher than 4, optimally less than 3.3, should be maintained for the gel component. Acidification is best accomplished through use of a phosphorus-based inorganic or organic acid. Where Carbomer is used as a gel structurant, pH can be as high as 7.5.

The second component of the oral compositions of the invention will preferably be a bicarbonate-containing opaque paste. Elements of this component are outlined below.

Advantageously, the bicarbonate will be the salt of an alkali metal such as sodium or potassium. Normally, the bicarbonate is included in the composition in an amount sufficient to provide a neutral or basic pH when the composition is contacted with water, preferably a pH of from 7.0 to 9.5, most preferably 8.0 to 9.0. Typically, the concentration will range from 0.5 to 80%, preferably from 5 to 50%, optimally between 8 and 20% by weight of the second semi-solid material.

A humectant and water system will normally be included. Humectants are usually polyols which, for example, may include glycerol, sorbitol, propylene glycol, lactitol, xylitol, polypropylene glycol, polyethylene glycol, hydrogenated corn syrup and mixtures thereof. Generally the amount of humectant will range from 25 to 90%, preferably from 40 to 70% by weight of the first or second semi-solid material. Particularly preferred is a liquid mixture of 3 to 30% water, 0 to 80% glycerol and/or 20 to 80% sorbitol.

A natural or synthetic thickening agent may be present in an amount from 0.1 to 10%, preferably 0.5 to 5% by weight of the second semi-solid material may be present. Thickeners may include hydroxypropyl methylcellulose, hydroxyethyl cellulose, sodium carboxymethyl cellulose, xanthan gum, tragacanth gum, karaya gum, arabic gums, Irish moss, starch, alginates and carrageenans.

Surfactants are normally also included in the semi-solid materials, especially the second component of the oral compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from 0.5 to 5% by weight of a respective semi-solid component.

An abrasive in addition to the bicarbonate will normally be included in the second component paste. Abrasives may be selected from water-insoluble alkali or alkaline earth metal salts of carbonate, aluminate and silicate. Especially preferred are silica, and alumina. Amounts of the abrasive will range from 5 to 80% by weight of a respective semi-solid component.

Sweetening agents such as saccharin, sodium cyclamate, aspartame, sucrose and the like may be included at levels from 0.1 to 5% by weight of a respective semi-solid component.

Other additives may also be incorporated into the oral compositions including preservatives, silicones and anti-gingivitis actives such as triclosan and stannous gluconates.

The following examples will more fully illustrate the embodiments of this invention. All parts, percentages and proportions referred to herein and in the appended claims are by weight of the total composition unless otherwise stated.

EXAMPLE 1

Typical of the present invention are paste and gel components whose formulations are detailed under Tables I and II.

TABLE I

Bicarbonate Paste Component

| INGREDIENT | WT. % |
| --- | --- |
| Polyol II (sorbitol and other sugars) | 48.70 |
| Syloid 63XX (abrasive silica) | 15.00 |
| Sodium Bicarbonate | 10.00 |
| PEG 32 (polyethylene glycol) | 5.00 |
| Sylox 15x (thickening silica) | 4.60 |
| Flavor | 1.00 |
| Tetrasodium Pyrophosphate | 0.50 |
| Sodium Lauryl Sulfate | 2.98 |
| SD Alcohol 38B | 2.85 |
| Cellulose Gum | 0.80 |
| Gantrez S-97 | 0.10 |
| Sodium Saccharin | 4.00 |
| Sodium Fluoride | 0.44 |
| Titanium Dioxide | 0.30 |
| Deionized Water | Balance |

TABLE II

Peroxide Gel Component

| COMPONENT | WT. % |
| --- | --- |
| Pluronic F127 | 20.00 |
| Glycerin | 20.00 |
| PEG-600 | 10.00 |
| PEG 1450 | 10.00 |
| Hydrogen Peroxide (35% food grade) | 4.285 |
| FD&C Blue | 0.005 |
| Phosphoric Acid (85% w/w) | 0.15 |
| Deionized Water | Balance |

EXAMPLE 2

Another set of formulations suitable for the present invention are the paste and gel components detailed under Tables III and IV.

TABLE III

| COMPONENT | WT. % |
| --- | --- |
| Sorbitol | 52.11 |
| Syloid 63XX (abrasive silica) | 15.00 |
| Sodium Bicarbonate | 15.00 |
| PEG 32 (polyethylene glycol) | 5.00 |
| Sylox 15x (thickening silica) | 4.00 |
| Sodium Lauryl Sulfate | 2.98 |
| SD Alcohol 38B | 2.85 |
| Gantrez AN-139 | 1.00 |
| Cellulose Gum | 0.80 |
| Sodium Saccharin | 0.50 |
| Sodium Fluoride | 0.46 |
| Titanium Dioxide | 0.30 |

TABLE IV

| COMPONENT | WT. % |
| --- | --- |
| Carbopol 940 (2% solution) | 20.00 |
| Glycerin | 40.00 |
| Hydrogen Peroxide | 4.30 |
| FD&C Blue | 0.005 |
| Sodium Hydroxide (50% soln) | adjusted to pH 7.0 |
| Deionized Water | Balance |

EXAMPLE 3

This example illustrates a paste and gel combination incorporating the anionic polymer in the gel, the formulations being detailed under Tables V and VI.

TABLE V

| INGREDIENT | WT. % |
| --- | --- |
| Polyol II (sorbitol and other sugars) | 45.25 |
| Sodium Bicarbonate | 20.00 |
| Calcium Carbonate | 15.00 |
| PEG 32 (polyethylene glycol) | 5.00 |
| Sodium Lauryl Sulfate | 3.00 |
| SD Alcohol 38B | 3.00 |
| Sodium Monofluorophosphate | 1.15 |
| Flavor | 1.00 |
| Cellulose Gum | 0.80 |
| Sodium Saccharin | 0.50 |
| Titanium Dioxide | 0.30 |
| Deionized Water | Balance |

TABLE VI

| COMPONENT | WT. % |
| --- | --- |
| Pluronic F127 | 25.00 |
| Glycerin | 25.00 |
| PEG 1450 | 10.00 |
| Hydrogen Peroxide (35% food grade) | 4.00 |
| Gantrez AN-116 | 1.00 |
| FD&C Blue | 0.005 |
| Phosphoric Acid (85% w/w) | 0.10 |
| Deionized Water | Balance |

EXAMPLE 4

This example illustrates a paste and gel combination incorporating an anionic polymer in the paste component as detailed under Tables VII and VIII.

TABLE VII

| INGREDIENT | WT. % |
| --- | --- |
| Sorbitol | 31.32 |
| Glycerin | 15.00 |
| Syloid 63XX (abrasive silica) | 15.00 |
| Sodium Bicarbonate | 15.00 |
| PEG 32 (polyethylene glycol) | 5.000 |
| Sylox 15x (thickening silica) | 4.60 |
| Sodium Lauryl Sulfate | 2.50 |
| SD Alcohol 38B | 2.50 |
| Gantrez S-97 | 2.00 |
| Cellulose Gum | 0.80 |
| Sodium Saccharin | 0.50 |
| Sodium Fluoride | 0.44 |
| Titanium Dioxide | 0.30 |
| Deionized Water | Balance |

TABLE VIII

| COMPONENT | WT. % |
| --- | --- |
| Pluronic F127 | 25.000 |
| Glycerin | 35.000 |
| Hydrogen Peroxide (35% food grade) | 10.00 |
| FD&C Blue | 0.005 |
| Phosphoric Acid (85% w/w) | 0.10 |
| Deionized Water | Balance |

EXAMPLE 5

A series of experiments were conducted to establish the performance benefits of synthetic linear anionic polycarboxylates to achieve closer uniformity of extrusion between two separate dentifrice streams of a dual compartment dispensing container. Base formulas for each of these streams are set forth under Table IX and X, respectively.

TABLE IX

| INGREDIENT | WEIGHT % |
| --- | --- |
| Polyol II (sorbitol and other sugars) | 47.14 |
| Syloid 63EXX | 15.00 |
| Sodium Bicarbonate | 10.00 |
| Deionized Water | 7.96 |
| PEG 32 (polyethylene glycol) | 5.00 |
| Sylox 15X | 6.00 |
| Sodium Lauryl Sulphate | 2.98 |
| SD Alcohol 38B | 2.84 |
| Flavor | 1.30 |

TABLE IX-continued

| INGREDIENT | WEIGHT % |
| --- | --- |
| Menthol | 0.50 |
| Sodium Saccharin | 0.54 |
| Sodium Fluoride | 0.44 |
| Titanium Dioxide | 0.30 |

TABLE X

| INGREDIENT | WEIGHT % |
| --- | --- |
| Glycerin | 40.00 |
| Deionized Water | 35.56 |
| Hydrogen Peroxide | 4.285 |
| FD&C Blue | 0.005 |
| Phosphoric Acid | 0.15 |
| Pluronic F-127 | 20.00 |

Dispensers of the type shown in the accompanying figure were separately charged with the formulations shown in Tables IX and X. Test 1B was utilized as a control and further included 0.8% carboxymethyl cellulose, all other bicarbonate phases were formulated without this component. Tests 2B through 5B with the bicarbonate phases included 1.0, 0.96, 0.70 and 0.40%, respectively, of Gantrez S-97. Levels of Polyol II were adjusted for changes in the Gantrez concentration. Selection of Gantrez S-97 for testing was based upon it being a typical synthetic linear anionic polycarboxylate.

Test 1P whose formula is shown under Table X served as a peroxide phase control. Under Tests 2P, 3P and 4P, amounts of Gantrez S-97 were incorporated at 1.0, 0.5 and 0.25%, respectively. Water levels were adjusted to accommodate for changes in the Gantrez level.

Streams of dentifrice from each of the Test formulas were placed into barrels of the dispenser shown in the FIGURE. Piston bottoms of these dispensers were then positioned against a stationary rod and placed within an Instron force measurement device. Actuation force necessary to extrude formula from the cylinder was then measured on the Instron equipment. Results are listed in Table XI.

TABLE XI

| TEST NO. | % GANTREZ S-97 | ACTUATION FORCE IN Kg |
| --- | --- | --- |
| Bicarbonate Phase | | |
| 1B | 0 | 5.72 |
| 2B | 1.0 | 3.59 |
| 3B | 0.96 | 3.95 |
| 4B | 0.70 | 4.38 |
| 5B | 0.40 | 3.98 |
| Peroxide Phase | | |
| 1P | 0 | 2.97 |
| 2P | 1.0 | 5.90 |
| 3P | 0.5 | 5.22 |
| 4P | 0.25 | 4.45 |

Table XI demonstrates that in the bicarbonate phase, Gantrez appears to enhance piston movement (i.e. less force necessary) as the polymer concentration increases. Concomitantly it was observed that not only does the phase flow better but an acceptable toothpaste consistency (will not leak out of pump) was still as retained. Although not meant to be bound by any theory, it appears that Gantrez operates to lubricate the formula relative to the piston walls. These results were unexpected.

Likewise in the peroxide phase, incorporation of Gantrez achieved a formula that began to match in actuation force those of the bicarbonate phases. For instance, compare Test 4B with 4P. Alternatively, Gantrez need only be placed in one of the phases. For instance, compare Test 1B with 2P wherein actuation forces are also essentially matched.

The foregoing description and Examples illustrate selected embodiments of the present invention and in light thereof various modifications will be suggested to one skilled in the art, all of which are within the spirit and purview of this invention.

What is claimed is:

1. A dental product comprising:
   (i) a dispensing container with an upper and a lower body which are telescopically engageable one with another, the upper body including at least two hollow and separate parallel cylinders, the cylinders having a first generally closed end and a second end telescopically and slidingly accommodating at least two parallel pistons which conform to ride sealingly along the interior walls of the cylinders so as to force any flowable materials to flow toward the first end of the cylinder upon relative compression of the cylinders and pistons, the cylinders having outlet channels;
   (ii) an outlet means in fluid communication with the outlet channels, the outlet means including adjacent outlet openings unconnected to each other and having means for causing the flowable materials to flow toward each other at the outlet openings to form a single, banded, unmixed stream;
   (iii) a first semi-solid flowable material and second semi-solid flowable material, the second semi-solid flowable material containing a bicarbonate salt, each of the first and second semi-solid materials being stored in separate ones of the at least two hollow parallel cylinders, and at least one of the semi-solid materials containing from 0.05 to 20% of a synthetic linear anionic polycarboxylate.

2. The dental product according to claim 1 wherein the polycarboxylate is a copolymer formed from monomers which in their acidic form are selected from the group consisting of acrylic, methacrylic, ethacrylic, succinic, maleic acids and mixtures thereof.

3. The dental product according to claim 1 wherein the polycarboxylate comprises a copolymer of vinyl methyl ether and maleic acid or anhydride.

4. The dental product according to claim 1 wherein the polycarboxylate is an alkali metal or ammonium salt of a copolymer of vinyl methyl ether and maleic acid or anhydride having a molecular weight of about 30,000 to 500,000.

5. The dental product according to claim 1 wherein at least one of the two semi-solid flowable materials further comprise a fluoride present in an effective amount to be an anti-caries agent.

6. The dental product according to claim 1 further comprising a peroxide which is selected from the group consisting of hydrogen peroxide, urea peroxide, percarbonate, perphosphate, persilicate, calcium peroxide and mixtures thereof.

7. The dental product according to claim 1 wherein the semi-solid material streams each have a viscosity ranging from 20,000 to 1,500,000 centipoise at 25° C.

* * * * *